United States Patent
Gronowski et al.

(10) Patent No.: US 10,384,957 B2
(45) Date of Patent: Aug. 20, 2019

(54) APPARATUS AND METHOD FOR DETECTING DEGASSED CATION CONDUCTIVITY

(71) Applicant: WALTRON BULL & ROBERTS, LLC, Flemington, NJ (US)

(72) Inventors: Uwe Gronowski, Berlin (DE); Yann Georges Louis Bouvier, Paladru (FR); Jonathan Connor Guy, Newtown, PA (US); Kenneth Then, High Bridge, NJ (US)

(73) Assignee: Waltron Bull & Roberts, LLC, Flemington, NJ (US)

( * ) Notice: Subject to any disclaimer, the term of this patent is extended or adjusted under 35 U.S.C. 154(b) by 247 days.

(21) Appl. No.: 15/611,417

(22) Filed: Jun. 1, 2017

(65) Prior Publication Data
US 2018/0346347 A1    Dec. 6, 2018

(51) Int. Cl.
| | | |
|---|---|---|
| *G01N 33/00* | (2006.01) | |
| *C02F 1/20* | (2006.01) | |
| *G01N 33/18* | (2006.01) | |
| *G01N 27/416* | (2006.01) | |
| *B01D 19/00* | (2006.01) | |
| *C02F 1/00* | (2006.01) | |
| *C02F 101/10* | (2006.01) | |

(52) U.S. Cl.
CPC ............ *C02F 1/20* (2013.01); *B01D 19/0005* (2013.01); *B01D 19/0063* (2013.01); *C02F 1/008* (2013.01); *G01N 27/4162* (2013.01); *G01N 33/1813* (2013.01); *C02F 2101/10* (2013.01); *C02F 2209/03* (2013.01); *C02F 2209/05* (2013.01); *C02F 2209/40* (2013.01); *C02F 2209/44* (2013.01); *C02F 2303/08* (2013.01)

(58) Field of Classification Search
CPC .. G01N 27/06; G01N 31/005; G01N 33/1846; G01N 27/4045; G01N 27/4162; G01N 33/1813; B01D 19/0005; B01D 19/0063; B01D 15/36; B01D 15/40; B01D 61/445; C02F 1/008; C02F 1/20; C02F 2101/10; C02F 2209/03; C02F 2209/05; C02F 2209/40; C02F 2209/44; C02F 2303/08
See application file for complete search history.

(56) References Cited

U.S. PATENT DOCUMENTS 6,228,325 B1 *   5/2001   Godec ................... G01N 27/06
                                                                422/80

\* cited by examiner

*Primary Examiner* — Sharon Pregler
(74) *Attorney, Agent, or Firm* — Volpe and Koenig, P.C.

(57) ABSTRACT

An apparatus for detecting cation conductivity of sample water is provided. The apparatus includes a decarbonation device which receives ambient air and removes $CO_2$ components from the ambient air to produce decarbonated ambient air. The apparatus also includes a desorption device which receives the decarbonated ambient air and sample water that includes $CO_2$ gas. The apparatus also includes one or more control processors which cause the decarbonated ambient air to be provided to the sample water in the desorption chamber where a portion of the $CO_2$ gas is removed from the sample water when the decarbonated air passes through the sample water. The desorption chamber utilizes gravity to implement counterflow of the sample water and the decarbonated air to efficiently produce degassed sample water. The degassed water is provided to a conductivity sensor for evaluating the corroding anionic impurities of the water.

20 Claims, 4 Drawing Sheets

US 10,384,957 B2

APPARATUS AND METHOD FOR DETECTING DEGASSED CATION CONDUCTIVITY

SUMMARY

The present application discloses apparatuses and methods for detecting cation conductivity of water via an automated degas process which efficiently removes $CO_2$ from sample water in a time period measured in seconds (e.g., about 45 seconds to about 90 seconds) rather than the 20-45 minute reboiler method time period.

A desorption device for use with detecting degassed cation conductivity is provided which includes a gas inlet port, a sample water inlet port and a desorption chamber extending between a bottom portion of the desorption device and a top portion of the desorption device. The top portion is located above the bottom portion relative to ground. The desorption chamber is configured to receive sample water that includes carbon dioxide ($CO_2$) gas via the sample water inlet port at the top portion of the desorption device and receive decarbonated ambient air via the gas inlet port at the bottom portion of the desorption device. The desorption chamber is also configured to hold the sample water in the desorption chamber at the bottom portion of the desorption device and produce degassed sample water by removing a portion of the $CO_2$ gas from the sample water held in the desorption chamber when the decarbonated ambient air passes through the sample water toward the top portion of the desorption device. The desorption chamber is further configured to provide a pathway, via a degassed water outlet port at the bottom of the desorption device, for the degassed sample water to flow from the desorption chamber.

An apparatus for detecting degassed cation conductivity is provided which includes a decarbonation device configured to receive ambient air and remove $CO_2$ components from the ambient air to produce decarbonated ambient air. The apparatus also includes a desorption device comprising a desorption chamber configured to receive the decarbonated ambient air and receive sample water comprising $CO_2$ gas. The apparatus also includes one or more control processors configured to cause the decarbonated ambient air to be provided to the sample water received into the desorption chamber and remove a portion of the $CO_2$ gas from the sample water when the decarbonated air passes through the sample water to produce degassed sample water.

A method of detecting degassed cation conductivity is provided which includes receiving, at a desorption device, sample water comprising $CO_2$ gas via a sample water inlet port at a top portion of the desorption device and receiving, at the desorption device, decarbonated ambient air via a gas inlet port at a bottom portion of the desorption device. The method also includes holding the sample water in a desorption chamber at the bottom portion of the desorption device and producing degassed sample water by removing a portion of the $CO_2$ gas from the sample water held in the desorption chamber when the decarbonated ambient air passes through the sample water toward the top portion of the desorption device. The method further includes providing the degassed sample water out of the desorption chamber via a degassed water outlet port at the bottom of the desorption device and measuring a conductivity of the degassed sample water.

BRIEF DESCRIPTION OF THE DRAWINGS

A more detailed understanding can be had from the following description, given by way of example in conjunction with the accompanying drawings wherein.

DETAILED DESCRIPTION

Figure 1:
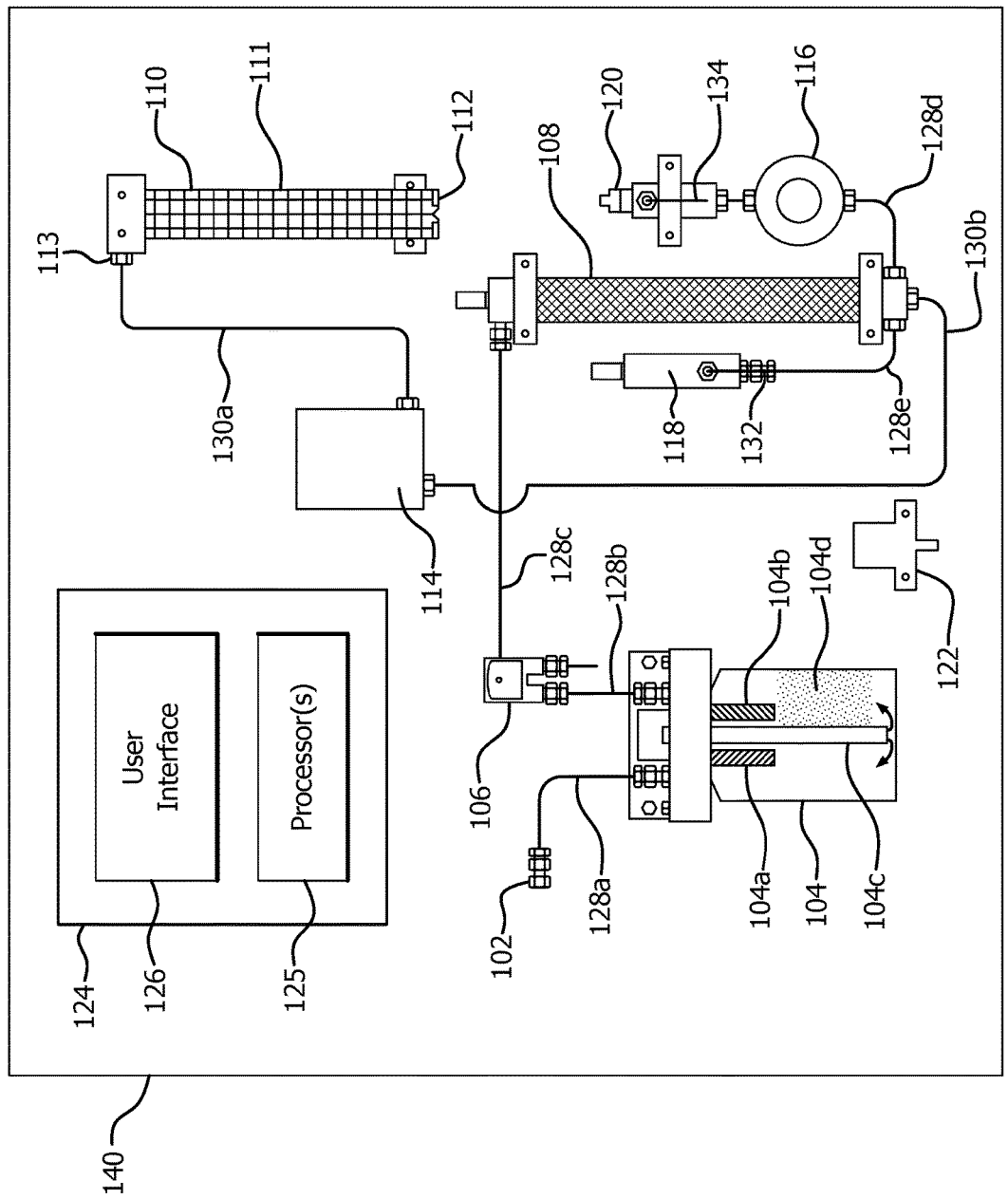
FIG. 1 is a block diagram of an example analyzer used to detect fluid conductivity according to embodiments disclosed herein.

Growth in renewable energy sources has placed greater burden on modern power electrical plants to cycle on and off to maintain steady and reliable electric power production between renewables and a level of demand on energy grid over a time period (e.g., 24 hours). For example, modern gas-fired electric plants typically utilize a combination of gas (70%) and steam (30%) turbines to produce electricity.

Steam turbines generate mechanical power from the energy of steam at high temperature and pressure. Impurities (e.g., chlorides and acetates) that are present in the water-steam circulation of the turbines, however, highly contribute to the water's corrosive potential over time. The impurities also contribute to scaling and pitting (e.g., resulting from chloride deposits on rotors, disks, blades and other components). Accordingly, the prevention of pipe and component corrosion and the protection of steam turbines from impurities are important aspects of quality assurance of water-steam circulation in power stations.

For example, the sample water to be used for the water steam circulation is monitored to detect the presence of harmful impurities (i.e., impurities contributing to corrosion, scaling and pitting). Based on the monitoring, it is determined during a start-up period of a cycle, whether the steam is "pure steam" (e.g., no harmful impurities or level of harmful impurities below a threshold level) to be sent to the steam turbine or bypassed to the condenser. The efficiency of a plant depends upon how quickly the pure steam reaches the second stage. For example, during a cycle in a gas-fired combined cycle plant, fuel is burned and excess heat is exhausted for 100% of the cycle while merely 70% (i.e., from the gas) of the power potential is achieved.

Because the harmful impurities in the water are conductive, cation conductivity measurements of the sample water are acquired to determine the presence of the harmful impurities in the water. The water typically includes impurities in the water, however, which contribute to the conductivity of the water but are far less harmful (i.e., contribute much less to corrosion potential) than ions of saline components, such as chloride and acetates. Accordingly, these less harmful impurities are removed from the sample water so that the measured conductivity of the sample water more accurately indicates the water's corrosive potential.

For example, sample water typically includes less harmful impurities, such as ammonium $NH_4^+$ ions, resulting from treated water conditioned with chemicals such as ammonia and caustic soda solution). These less harmful impurities in the sample water are removed from the sample water by passing the sample water through a resin in a cation exchanger.

The sample water also typically includes $CO_2$ (e.g., resulting from leaks in the water-steam circuit and the turbine condenser during the start-up period) which contributes to the conductivity of the water but contributes to the water's corrosive potential much less than the more harmful impurities.

Conventional methods for removing $CO_2$ from the water include using of a reboiler to heat the sample and expel the $CO_2$. These reboiler methods provide useful results (i.e., removing over 90% of the $CO_2$ from the water) for evaluating the corrosive potential of the water. These reboiler methods are highly inefficient, however, typically requiring 20 minutes to 45 minutes to achieve these useful results, causing a time delay for loading the steam turbine which negatively impacts the efficiency of the plant.

The present application discloses apparatuses and methods for detecting cation conductivity of water via an automated degas process which efficiently removes about 92% to about 94% of the $CO_2$ from the sample water in a time period measured in seconds (e.g., time period of about 45 seconds to about 90 seconds) rather than the 20-45 minute reboiler method time period. Accordingly, in the 20-45 minutes of start-up time saved using the automated degas process described herein, the typical combined cycle plant generates more income from the same fuel consumed with each start-up (and even more income using typical "peak" electricity pricing). Further, the automated degas process described herein conserves more energy and reduces heat and exhaust emissions which negatively impact the environment.

Other conventional methods for removing $CO_2$ from the water sample include supplying pressurized bottled gasses to the water to remove the $CO_2$. While these methods can remove $CO_2$ in less time than reboiler methods, these methods are also inefficient and hazardous. For example, the pressurized bottles are costly, use up storage space, include time to replace the bottles and can be hazardous due to the pressurized gas on site. The degas process described in the present application utilizes ambient air to produce an inert gas (i.e., decarbonated ambient air) which removes the $CO_2$ by passing the decarbonated ambient air through the sample water using gravity and counterflow. Accordingly, the automated degas process described herein provides useful results for evaluating the corrosive potential of the water while reducing costs, saving time and avoiding hazardous conditions.

FIG. 1 is a block diagram of an example analyzer 100 used to detect fluid conductivity according to embodiments disclosed herein. As shown in FIG. 1, the analyzer 100 includes sample inlet 102, cation exchanger 104, flow meter 106, desorption device 108, decarbonation device 110, air inlet 112, gas pump 114, circulation pump 116, overflow device 118, degassed water conductivity sensor 120, drain 122, electronics housing 124, user interface 126, water conduits 128a-128e (e.g., pipes), gas conduits 130a and 130b, and water outlet conduits 132 and 134. The sizes, shapes and locations of each of the components shown in FIG. 1 are merely exemplary. Apparatuses used to detect conductivity of sample water can include components having sizes, shapes and locations different from those shown in FIG. 1. As shown in FIG. 1, the analyzer also includes a mounting plate 140 to which components of the analyzer 100 are mounted.

Electronics housing 124 is configured to house electronic and processing components used to control operation of the components and to communicate between the components described herein. Electronic and processing components include, for example, one or more processors 125 and other components (not shown) such as memory, circuitry, wires, buses, transmitters, receivers and network interfaces. The electronic and processing components may be configured to communicate (wired or wirelessly) with components of analyzer 100. Additionally one or more electronic and processing components, such as one or more additional control processors (not shown), can be located at one or more of the components of the analyzer and configured to communicate with the electronic and processing components housed at electronics housing 124. The one or more control processors 125 are configured to process instructions (e.g., from user input and predefined programmed instructions).

As shown in FIG. 1, user interface 124 (e.g., touch screen display) is disposed at electronics housing 124. User interface 124 may be disposed at a location separate from electronics housing. User interface 124 is used to display operating conditions (e.g., conductivity measurements, flow rate, water temperature, ambient air temperature and water pressure) of analyzer 100. User interface 124 is also configured to receive user input for selecting parameters (e.g., numerical values) for setting operating conditions of components of the analyzer.

Arrows are used in FIG. 1 to illustrate the flow of sample water and gas (e.g., decarbonated air) through components of the analyzer 100. As shown in FIG. 1, sample water flows from sample inlet 102 to cation exchanger 104 via water conduit 128a. The sample water received at cation exchanger 104 is typically treated water (i.e., water which has been conditioned with chemicals, such as ammonia and/or caustic soda solution). The treated water includes impurities (e.g., ammonium NH4+ ions) which contribute to the conductivity of the water, but contribute much less to the corrosive potential of the water than other more harmful impurities, such as acid producing anions such as chlorides and acetates.

The cation exchanger 104 includes specific conductivity sensor 104a, cation conductivity sensor 104b and water conduit 104c. As the sample water passes through conduit 104c, sample water flows (indicated by the left arrow in the cation exchanger 104) to a section of the cation exchanger 104 where the specific conductivity sensor 104a detects the total dissolved solids in the sample water.

Sample water also flows (indicated by the right arrow in the cation exchanger 104) to a section of the cation exchanger 104 having a resin 104d which removes the ions (e.g., ammonium NH4+ ions) from the treated sample water and where the cation conductivity sensor 104b detects the cation conductivity of the treated sample water. That is, the cation conductivity sensor 104b detects the cation conductivity of the sample water after the less harmful impurities are removed from the sample water to more accurately determine the water conductivity due to the presence of the more harmful impurities (e.g., acid producing anions such as chlorides and acetates) in the sample water.

The sample water exiting the cation exchanger 104 flows to flow meter 106 which determines a flow rate of the sample water passing through the flow meter 106 and supplied to desorption device 108. A pH value of the sample water exiting the cation exchanger 104 is determined based on the detected specific conductivity and the detected cation conductivity of the water.

In addition to the ions (e.g., ammonium NH4+ ions) removed by the cation exchanger, the sample water also includes other impurities (i.e., organic components) which contribute to water conductivity but contribute much less to the corrosive potential of the water than the more harmful impurities. For example, air can penetrate (e.g., via leaks in the water-steam circuit and via the turbine condenser during a turbine start-up period) the steam turbine system. While oxygen and nitrogen and other trace gases in the air physically dissolve and do not form ions or contribute to water conductivity, $CO_2$ chemically dissolves into ions in the circulating water and contributes to the water conductivity.

The chemical reactions of $CO_2$ in the water are shown by the following equations:

$$CO_2 + 2H_2O \leftrightarrow HCO_3^- + H_3O^+ \quad (pK=6.3) \quad \text{Equation 1}$$

$$HCO_3^- + 2H_2O \leftrightarrow CO_3^{2-} \quad (pK=10.3) \quad \text{Equation 2}$$

where pK is the logarithmic value of the dissociation constant K. The chemical equilibrium state of the chemical reactions is pH dependent. At a pH value of 5.0, about 94% of the $CO_2$ in the water exists as $CO_2$ gas and about 6% of the $CO_2$ exists as carbonate ions $HCO_3^-$. The pH value of the water exiting the cation exchanger 104 is typically in the range of about 5.5 to about 6.0. Accordingly, the $CO_2$ content of the sample water exiting the cation exchanger 104 is primarily $CO_2$ gas and the bicarbonate ion, $CO_3(2-)$, is miniscule, which renders the $CO_2$ to be much less harmful to corrosion than the ions of salt containing components. Because $CO_2$ contributes to the conductivity of the water, however, the $CO_2$ causes artificially high conductivity measurements for evaluating corroding anionic impurities of the water.

To provide more accurate conductivity measurements for detecting the presence of the harmful impurities contributing to the corrosive potential of the water, the $CO_2$ is removed from the sample water through an efficient degas procedure. For example, referring again to FIG. 1, analyzer 100 includes components (e.g., degas assembly components) configured to remove a large portion of the $CO_2$ (e.g., a range of about 92% to about 95% of the $CO_2$) from the sample water in a time period ranging from about 45 seconds to about 90 seconds.

As shown in FIG. 1, exemplary degas assembly components include desorption device 108, decarbonation device 110, gas pump 114, circulation pump 116 and overflow device 118. Water conduits 128d and 128e and gas conduits 130a and 130b couple the degas assembly components and provide water and gas pathways between degas assembly components.

Decarbonation device 110 comprises an air inlet port 112, a gas outlet port 113 and a decarbonation chamber 111 configured to receive ambient air via the air inlet port 112 and provide decarbonated ambient air via the gas outlet port 113. The decarbonation chamber 111 includes decarbonation material (not shown), such as soda lime, used to remove $CO_2$ from the ambient as the ambient air passes through the material. The top of the decarbonation device 110 is above the bottom of the decarbonation device 110 relative to ground and the air inlet port is disposed at the bottom of the decarbonation device 110 to facilitate the flow of the ambient air received via the air inlet port 112 toward the gas outlet port 113. As the ambient air passes through the decarbonation material, $CO_2$ is removed from the ambient air to produce decarbonated air.

Gas pump 114 is configured to facilitate the flow of the decarbonated ambient air between decarbonation device 110 and desorption device 108 via gas conduits 130a and 130b. The decarbonated air is provided from the decarbonation device 110 to gas pump 114 via gas conduit 130a and from gas pump 114 to desorption device 108 via gas conduit 130b.

While the decarbonated air is being provided to desorption device 108, the sample water from the cation exchanger 104 is also provided to the desorption device 108 via flow meter 106 and water conduit 128b. The flow meter 106 determines a flow rate of the sample water being supplied to the desorption device 108. The flow rate determined from flow meter 106 can also be compared to a flow rate threshold range (e.g., 5.0 liters per hour to 8 liters per hour). The flow rate threshold can be a predetermined threshold for a particular degas assembly according to different factors, such as operating conditions (e.g., water temperature, ambient temperature, water pressure) and size of the assembly components (e.g., desorption device 108). The flow rate threshold can also be automatically determined and adjusted during operation. If the flow rate is less than or equal to the bottom flow rate (e.g., 5.0 liters per hour) of the flow rate threshold range, then the degas procedure is not implemented (e.g., operation of one or more degas assembly components is stopped). Otherwise, the sample water is provided, via water conduit 128c, to desorption device 108.

Figure 2:
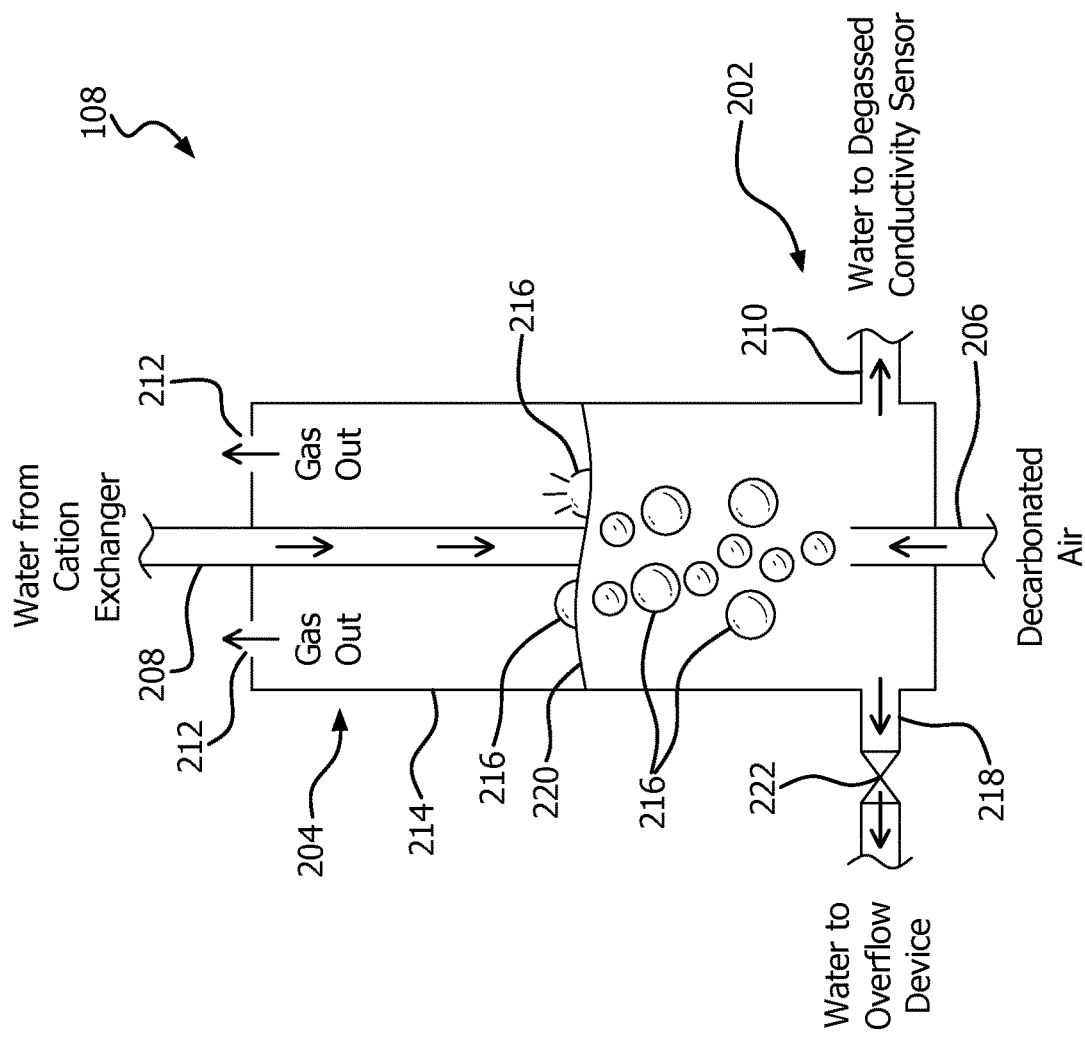
FIG. 2 is a sectional view of an exemplary desorption device illustrating a degas process according to embodiments described herein.

FIG. 2 is a sectional view of desorption device 108 illustrating an exemplary degas process according to embodiments described herein. As shown in FIG. 2, the desorption device 108 includes a desorption chamber 214 extending between a bottom portion 202 of the desorption device 108 and a top portion 204 of the desorption device 108. The top portion 204 is above the bottom portion 202 relative to ground (not shown). The desorption device 108 includes a decarbonated air inlet port 206, a degassed water outlet port 210 and a water overflow outlet port 218 at the bottom portion 202 of the desorption device 108. The desorption device 108 also includes a sample water inlet port 208 and gas outlet ports 212 at the top portion 204 of the desorption device 108.

As shown in FIG. 2, the desorption device 108 includes a water overflow valve 222 configured to control the flow of the sample water exiting the desorption chamber 214 via the water overflow outlet port 218 and adjust the water pressure in the desorption chamber 214. For example, one or more control processors 125 may receive an indication of the flow rate of the water detected by flow meter 106 and control the valve 222 to adjust the water pressure in the desorption chamber 214 based on the flow rate of the sample water provided to the desorption chamber 214. In some embodiments, the water overflow valve 222 is connected to the desorption device 108. In other embodiments, a water overflow valve can be located downstream from the desorption device 108. In some embodiments, multiple valves are used to control a pathway for the water to exit the desorption chamber 214 via the water overflow outlet port 218.

The locations of the ports shown in FIG. 2 are merely exemplary. For example, ports 206, 210 and 218 can be disposed at locations at the bottom portion 202 of the desorption device 108 that are different from the locations shown in FIG. 2. Ports 208 and 212 can be disposed at locations at the top portion 204 of the desorption device 108 that are different from the locations shown in FIG. 2. The number of ports 206, 208, 210, 212 and 218 shown in FIG. 2 is also exemplary. For example, the sample water may enter the desorption chamber 214 via a plurality of sample water inlet ports 208 and a single gas outlet port 212.

As described above, the top portion 204 of the desorption device 108 is above the bottom portion of the desorption device 108 relative to ground (not shown). Accordingly, as shown in FIG. 2, gravity is utilized such that the sample water flows through the sample water inlet port 208 into the desorption chamber 214 in a first direction (indicated by arrows pointing down in FIG. 2) toward the bottom of the desorption device 108 (i.e., toward ground). The sample water accumulates and is held in the desorption chamber 214 at the bottom 202 of the desorption device 108. The decarbonated air is received in the desorption chamber 214, via the decarbonated air inlet port 206, in a second direction (indicated by arrows pointing up in FIG. 2) opposite the first direction.

As the decarbonated air is provided to the sample water, the decarbonated ambient air and the $CO_2$ gas flow, as bubbles 216 in FIG. 2, in the second direction through the sample water across water surface 220 and then toward gas outlet ports 212 at the top portion 204 of the desorption device 108. Accordingly, a portion of the $CO_2$ gas is driven off from the sample water where it escapes the desorption device 108 via the gas outlet ports 212, resulting in degassed sample water which includes sail-like or acid-like ions and organic components, as well as oxygen and nitrogen which do not form ions in the sample water.

The desorption device 300 is configured to prevent diffusion of $CO_2$, present in the ambient air adjacent to the desorption device 108, into the desorption chamber 214 while the decarbonated ambient air and the $CO_2$ gas flow out of the desorption chamber 214 via the gas outlet ports 212. The positive pressure of both the water and the decarbonized gas entering the chamber prevents ambient $CO_2$ from diffusing into the desorption chamber 214.

The desorption device 108 also includes a water overflow outlet port 218 disposed at the bottom portion 202 of the desorption device 108 and a water overflow valve 222 disposed at the water overflow outlet port 218. When the valve 222 is open, the sample water held in the desorption chamber 214 may flow from the desorption chamber 214 along an overflow pathway via the water overflow outlet port 218 and water conduit 128e to the overflow device 118. The overflow valve 222 is used to adjust the overflow pathway for a portion of the sample water to flow from the desorption device 108. The valve may be adjusted to various opening degrees between an open and closed position to adjust the water pressure in the desorption chamber 214.

The desorption device 108 also includes a degassed water outlet port 210 disposed at the bottom portion 202 of the desorption device 108. The degassed sample water flows, via the degassed water outlet port 210 and conduit 128d, from the desorption device 108 to water circulation pump 116, which is configured to facilitate the flow of the degassed sample water from the desorption device 108 to the degassed water conductivity sensor 120. The degassed water can then be provided to drain 122 via degassed sample water outlet 134.

The water pressure in the desorption chamber 214 may be adjusted according to the flow rate of the sample water detected by the flow meter 106. For example, one or more control processors 125 may receive an indication of the flow rate detected by the flow meter and control the pressure of the sample water in the desorption chamber 214 to maintain a flow rate (e.g., between a range of about 5 liters per hour to about 8 liters per hour) by controlling the water overflow valve 222 to adjust the overflow pathway. The overflow water can then be provided from water overflow device to the drain 122 via overflow water outlet 132.

In addition to valve 222, the circulating pump 116 may also be used to maintain the flow rate of the sample water in the desorption chamber 214. For example, in response to receiving an indication of the flow rate detected by the flow meter, the one or more control processors 125 may adjust the operating parameters of the circulating pump 116 to control the amount of water being provided to the circulating pump 116 via degassed water outlet port 210 and conduit 128d. Accordingly, the pressure of the sample water in the desorption chamber 214 can be adjusted to maintain the flow rate.

The portion of the $CO_2$ gas removed from the sample water in the desorption chamber 214 comprises a portion range of about 92% to about 95% of the $CO_2$ gas (i.e., degassing efficiency). Further, the portion of the $CO_2$ gas is removed during a degassing residence time period, which includes a time range of about 45 seconds to about 90 seconds from when the sample water enters the desorption chamber 214 to when the degassed sample water exits the desorption chamber 214.

The degassed sample water is measured by degassed water conductivity sensor 120. The conductivity measurements of the degassed water provide more accurate conductivity measurements for detecting the presence of the harmful impurities which contribute to the corrosive potential of the water.

Figure 3:
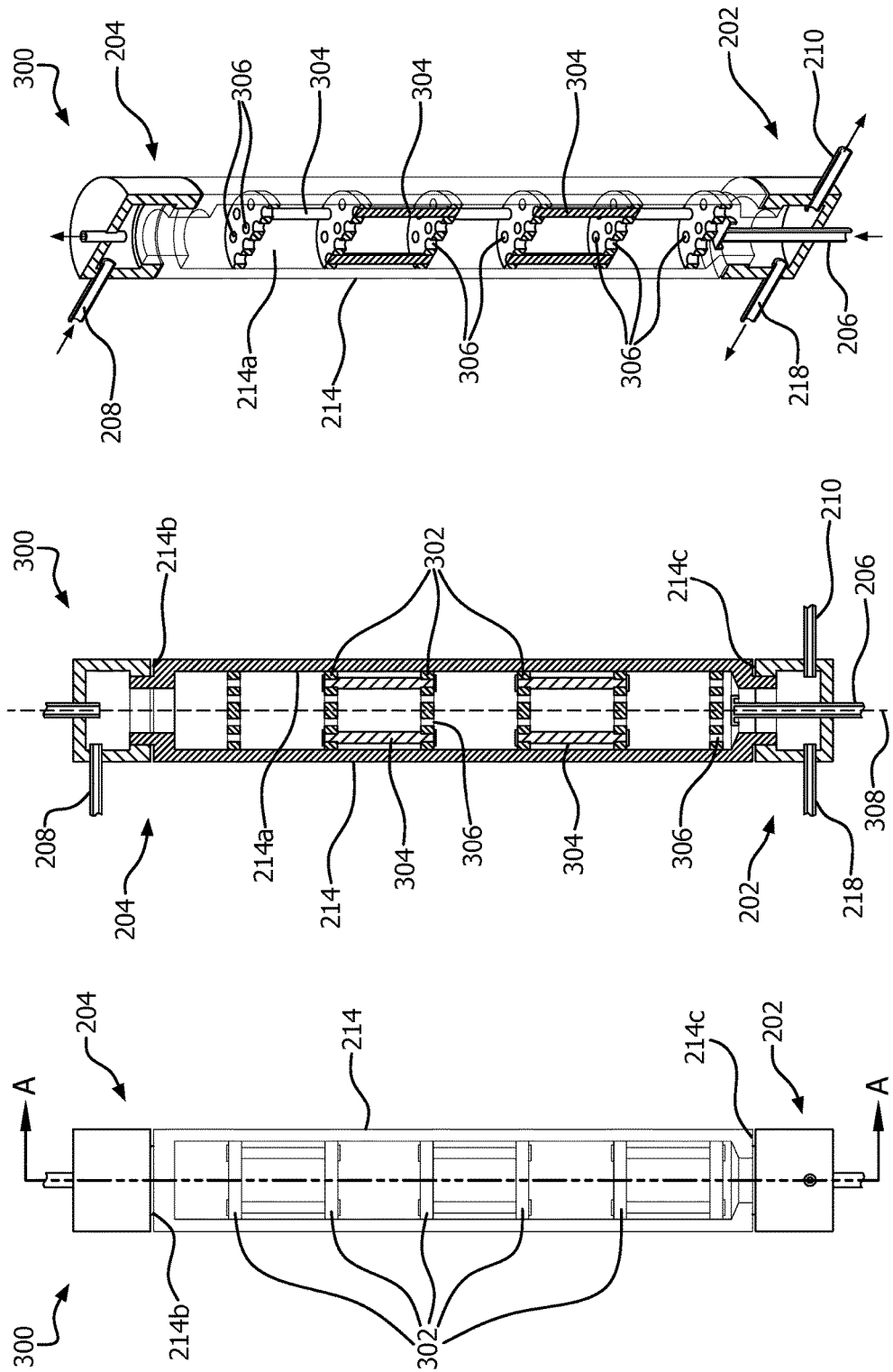
FIG. 3A is a partially exposed front view of an example desorption device for implementing a degas process according to embodiments described herein.
FIG. 3B is a cross sectional view of the example desorption device shown in FIG. 3A.
FIG. 3C is a perspective, cross sectional view of the example desorption device shown in FIG. 3A.

FIGS. 3A-3C are views of an example desorption device 300, including a plurality of tiered splash guards 302, for implementing a degas process according to embodiments described herein. FIG. 3A is a partially exposed front view of the example desorption device 300. FIG. 3B is a cross sectional view along section A-A of the exemplary desorption device 300 shown in FIG. 3A. FIG. 3C is a perspective, cross sectional view along section A-A of the example desorption device 300 shown in FIG. 3A.

Referring generally to FIGS. 3A-3C, the desorption desorption device 300 includes components similar to the components of the desorption desorption device 108 (shown in FIG. 2), such as desorption chamber 214, decarbonated air inlet port 206, degassed water outlet port 210 and water overflow outlet port 218 at the bottom portion 202 of the desorption device 300 and sample water inlet port 208 at the top portion 204 of the desorption device 300. In contrast to the multiple gas outlet ports 212 shown in FIG. 2, however, the desorption desorption device 300 includes a single gas outlet port 212 at the top portion 204 of the desorption device 300.

As shown in FIGS. 3A-3C, the desorption device 300 also includes a plurality of splash guards 302, each spaced from each other and extending perpendicular to center axis 308. The number, location and thickness of the layers shown in FIGS. 3A-3C are merely exemplary. Desorption devices can include any number of splash guards having different thicknesses (including equal thicknesses and unequal thicknesses). The splash guards 302 shown in FIGS. 3A-3C are spaced from each other at equal distances. Desorption devices can, however include splash guards spaced from each other at unequal distances such that some splash guards are closer to each other than other splash guards. As shown in FIGS. 3A-3C, the splash guards 302 are in contact with an inner side wall 214a of the desorption chamber 214. Portions of splash guards can, however, be distanced from the inner side wall 214a such that the water flows between the inner side wall 214a and the splash guards 302.

The splash guards 302 comprise a porous material (e.g., steel wool), including holes 306, configured to create a path for the water to flow toward the bottom portion 202 of the desorption chamber 300 while distributing the water across the porous material of each splash guards 302. The splash guards 302 break the water flow up into smaller fractions and reduce the level of water splashes, facilitating the degassing process. The water surface 220 contacts the coarse layer material of the splash guards, maximizing the surface area for the $CO_2$ to be removed from the water As shown in FIGS. 3A-3C, the desorption device 300 also includes a plurality of spacers 304 coupled to and extending between adjacent splash guards 302. The spacers are configured to provide support and limit movement of the support splash guards 302 as the water flows through the splash guards 302.

As shown in FIG. 3C, the desorption chamber 300 is cylindrical. Also, the desorption chamber 300 is defined by the inner side wall 214a, an inner top wall 214b and an inner bottom wall 214c. Desorption chambers may also include other shapes different from a cylinder, such as for example, a prism (e.g., rectangular prism, triangular prism) or a cone.

Figure 4:
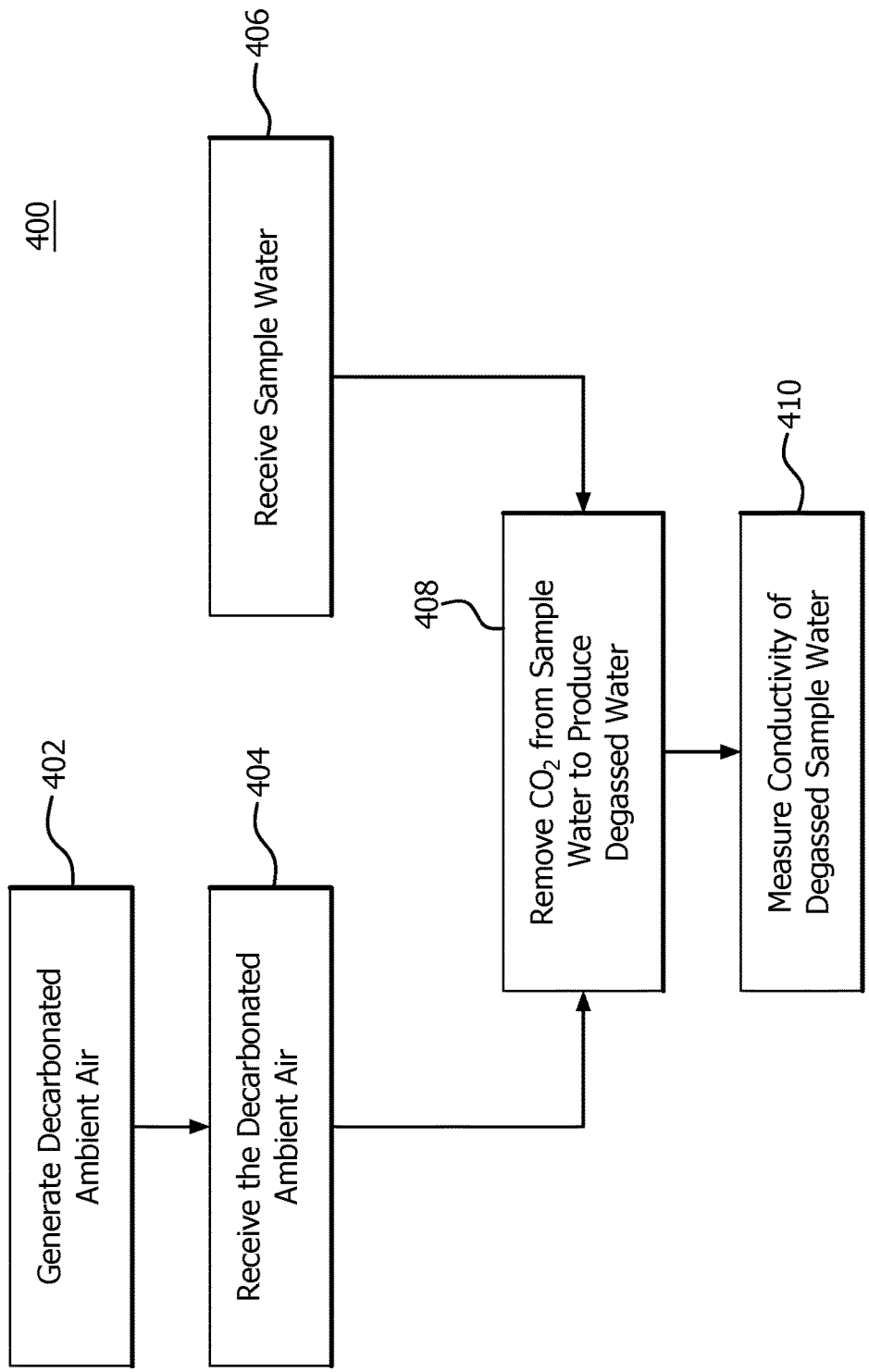
FIG. 4 is a flow diagram illustrating an example method of detecting cation conductivity according to embodiments described herein.

FIG. 4 is a flow chart illustrating an example method 400 of detecting degassed fluid conductivity. As shown at block 402 of FIG. 4, the method 400 includes generating decarbonated ambient air. For example, the decarbonated ambient air is generated by receive ambient air adjacent into a decarbonation chamber of a decarbonation device by passing the ambient air through a material such as soda lime to remove $CO_2$ components from the ambient air.

As shown at block 404 of FIG. 4, the method 400 includes receiving the decarbonated ambient air at the desorption device. The sample water which includes the $CO_2$ gas is also received at the desorption device at block 406 of FIG. 4. The sample water flows downward, due to gravity, and is held at a bottom of the desorption chamber.

The decarbonated ambient air, received at the bottom of the desorption chamber, is provided to the sample water. A portion of the $CO_2$ gas in the sample water is driven off from the sample water to produce degassed sample water, as shown at block 408. The decarbonated ambient air and the portion of the $CO_2$ gas driven off from the sample water flow upward across the surface of the water and and escape out of a top of the desorption chamber. The conductivity of the degassed sample water is then measured as shown at block 410.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. A desorption device for use with detecting degassed cation conductivity, the desorption device comprising:
   a gas inlet port;
   a sample water inlet port;
   a desorption chamber extending between a bottom portion of the desorption device and a top portion of the desorption device located above the bottom portion relative to ground, the desorption chamber configured to:
   receive sample water comprising carbon dioxide ($CO_2$) gas via the sample water inlet port at the top portion of the desorption device;
   receive decarbonated ambient air via the gas inlet port at the bottom portion of the desorption device;
   hold the sample water in the desorption chamber at the bottom portion of the desorption device;
   produce degassed sample water by removing a portion of the $CO_2$ gas from the sample water held in the desorption chamber when the decarbonated ambient air passes through the sample water toward the top portion of the desorption device; and
   provide a pathway, via a degassed water outlet port at the bottom of the desorption device, for the degassed sample water to flow from the desorption chamber.

2. The desorption device of claim 1, wherein
   the sample water flows in the desorption chamber in a first direction toward the bottom of the desorption device,
   the decarbonated ambient air and the $CO_2$ gas each flow in the desorption chamber in a second direction opposite the first direction toward a gas outlet port at the top portion of the desorption device,
   and the decarbonated ambient air and the $CO_2$ gas each pass through a surface of the sample water held in the desorption chamber and flow out of the desorption chamber via the gas outlet port.

3. The desorption device of claim 2, wherein the desorption device is further configured to prevent diffusion of $CO_2$ in the air into the desorption chamber while the decarbonated ambient air and the $CO_2$ gas each flow out of the desorption chamber via the gas outlet port.

4. The desorption device of claim 1, wherein the desorption chamber further comprises:
   a water overflow outlet port disposed at the bottom portion of the desorption device at a location different from the degassed water outlet port; and
   a water overflow valve configured to adjust an overflow pathway for the sample water to flow from the desorption device,
   wherein a water pressure in the desorption chamber is controlled (i) via the water overflow valve and (ii) a flow rate of the degassed sample water flowing from the desorption chamber via the degassed water outlet port.

5. The desorption device of claim 1, wherein the portion of the $CO_2$ gas removed from the sample water comprises a portion range of about 92% to about 95% of the $CO_2$ gas, and a period of time from when the sample water enters the desorption chamber to when the degassed sample water exits the desorption chamber comprises a time range of about 45 seconds to about 90 seconds.

6. An apparatus for detecting degassed cation conductivity, the apparatus comprising:
a decarbonation device configured to:
receive ambient air; and
remove carbon dioxide ($CO_2$) components from the ambient air to produce decarbonated ambient air;
a desorption device configured to:
receive the decarbonated ambient air; and
receive sample water comprising $CO_2$ gas;
one or more control processors configured to cause the decarbonated ambient air to be provided to the sample water received in the desorption device and remove a portion of the $CO_2$ gas from the sample water when the decarbonated air passes through the sample water to produce degassed sample water; and
a degassed water conductivity sensor configured to detect a conductivity of the degassed sample water.

7. The apparatus of claim 6, wherein the portion of the $CO_2$ gas removed from the sample water comprises a portion range of about 92% to about 95% of the $CO_2$ gas.

8. The apparatus of claim 6, wherein
the decarbonation device comprises:
an air inlet port;
a decarbonation chamber configured to receive the decarbonated ambient from the air inlet port and remove $CO_2$ from the ambient air to produce decarbonated air; and
a decarbonated air outlet port configured to provide a gas pathway for the decarbonated air from the decarbonation chamber; and
the desorption device comprises:
a gas inlet port at a bottom portion of the desorption device;
a sample water inlet port at a top portion of the desorption device, the top portion located above the bottom portion relative to ground; and
a desorption chamber extending between the bottom portion and the top portion, the desorption chamber configured to:
receive the sample water comprising the $CO_2$ gas via the sample water inlet port and hold the sample water at the bottom portion; and
receive decarbonated ambient air via the gas inlet port at the bottom portion of the desorption device.

9. The apparatus of claim 8, wherein a period of time from when the sample water enters the desorption chamber to when the degassed sample water exits the desorption chamber comprises a time range of about 45 seconds to about 90 seconds.

10. The apparatus of claim 8, wherein
the sample water flows in the desorption chamber in a first direction toward the bottom of the desorption device,
the decarbonated ambient air and the $CO_2$ gas each flow in the desorption chamber in a second direction opposite the first direction toward a gas outlet port at the top portion of the desorption device, and
the decarbonated ambient air and the $CO_2$ gas each pass through a surface of the sample water held in the desorption chamber and flow out of the desorption chamber via the gas outlet port.

11. The apparatus of claim 8, further comprising a flow meter configured to detect a flow rate of the sample water supplied to the desorption chamber,
wherein the one or more control processors are further configured to receive an indication of the flow rate detected by the flow meter and maintain the flow rate within a flow rate range by controlling a water pressure in the desorption chamber.

12. The apparatus of claim 11, wherein
the desorption chamber further comprises a degassed water outlet port disposed at the bottom portion of the desorption device configured to provide a degassed water pathway for the degassed water to flow to the degassed water conductivity sensor,
a water circulation pump configured to control a degassed water flow rate of the degassed sample water provided from the the desorption chamber to the degassed water conductivity sensor, and
the one or more control processors are further configured to control the water pressure in the desorption chamber by controlling an operation of the water circulation pump.

13. The apparatus of claim 11, wherein the desorption device further comprises:
a water overflow outlet port disposed at the bottom portion of the desorption device configured to provide a water overflow pathway for the sample water to flow from the desorption chamber; and
a water overflow valve disposed at the water overflow outlet port and configured to adjust the water overflow pathway.

14. The apparatus of claim 11, wherein the one or more control processors are further configured to prevent the degassed sample water from being produced when the flow rate is less than a bottom flow rate of the flow rate range.

15. The apparatus of claim 11, wherein the flow rate range is about 5.0 liters per hour to 8 liters per hour.

16. A method of detecting degassed cation conductivity, the method comprising:
receiving, at a desorption device, sample water comprising carbon dioxide ($CO_2$) gas via a sample water inlet port at a top portion of the desorption device;
receiving, at the desorption device, decarbonated ambient air via a gas inlet port at a bottom portion of the desorption device;
holding the sample water in a desorption chamber at the bottom portion of the desorption device;
producing degassed sample water by removing a portion of the $CO_2$ gas from the sample water held in the desorption chamber when the decarbonated ambient air passes through the sample water toward the top portion of the desorption device;
providing the degassed sample water out of the desorption chamber via a degassed water outlet port at the bottom of the desorption device; and
measuring a conductivity of the degassed sample water.

17. The method of claim 16, further comprising:
detecting a flow rate of the sample water received at the desorption device; and
maintaining the flow rate within a flow rate range by controlling, via one or more control processors, a water pressure in the desorption chamber.

18. The method of claim 17, wherein the water pressure in the desorption chamber is controlled by adjusting a water overflow valve to adjust a water overflow pathway via an overflow outlet port at the bottom of the desorption device.

19. The method of claim 17, wherein the water pressure in the desorption chamber is controlled by controlling an operation of a water circulation pump which adjusts a water flow rate of the degassed sample water provided from the desorption chamber via the degassed water outlet port.

20. The method of claim 16, wherein
the portion of the $CO_2$ gas removed from the sample water comprises a portion range of about 92% to about 95% of the $CO_2$ gas, and
a period of time from when the sample water enters the desorption chamber to when the degassed sample water exits the desorption chamber comprises a time range of about 45 seconds to about 90 seconds.

* * * * *